(12) United States Patent
Julien et al.

(10) Patent No.: US 7,892,575 B2
(45) Date of Patent: Feb. 22, 2011

(54) ORODISPERSIBLE PHARMACEUTICAL COMPOSITION FOR OROMUCOSAL OR SUBLINGUAL ADMINISTRATION OF AGOMELATINE

(75) Inventors: Mark Julien, Sigloy (FR); Jean-Manuel Pean, Orleans (FR); Francois Tharrault, Orleans (FR); Patrick Wuthrich, Orleans (FR)

(73) Assignee: Les Laboratoires Servier, Suresnes Cedex (FR)

( * ) Notice: Subject to any disclaimer, the term of this patent is extended or adjusted under 35 U.S.C. 154(b) by 989 days.

(21) Appl. No.: 11/638,960

(22) Filed: Dec. 14, 2006

(65) Prior Publication Data
US 2007/0134331 A1 Jun. 14, 2007

(30) Foreign Application Priority Data
Dec. 14, 2005 (FR) .................................. 05 12647

(51) Int. Cl.
 *A61K 9/00* (2006.01)
 *A61K 9/20* (2006.01)
 *A61K 9/26* (2006.01)
 *A61K 9/14* (2006.01)
(52) U.S. Cl. .................. 424/465; 424/400; 424/464; 424/472; 424/474; 424/489
(58) Field of Classification Search ................ None
See application file for complete search history.

(56) References Cited

U.S. PATENT DOCUMENTS

| 6,723,348 | B2 * | 4/2004 | Faham et al. | 424/490 |
| 6,770,368 | B2 * | 8/2004 | Luhn | 428/403 |
| 2005/0131071 | A1 * | 6/2005 | Wuthrich et al. | 514/630 |
| 2005/0182276 | A1 * | 8/2005 | Souvie et al. | 564/123 |

FOREIGN PATENT DOCUMENTS

| EP | 1467724 | 10/2004 |
| FR | 2834890 | 7/2003 |

OTHER PUBLICATIONS

Loo et al. Determination of the dose of agomelatine, a melatoninergic agonist and selective 5-HT (2C) antagonist, in the treatment of major depressive disorder: placebo-controlled dose range study, Int. Clin Psychopharmacol, 2002, 17, 239-247 (abstract only).*
French Preliminary Search Report for FR0512647 of Aug. 1, 2006.

* cited by examiner

*Primary Examiner*—Robert A Wax
*Assistant Examiner*—Melissa S Mercier
(74) *Attorney, Agent, or Firm*—Hueschen and Sage

(57) ABSTRACT

The invention relates to a coated solid orodispersible pharmaceutical composition for the administration of agomelatine by the oral, oromucosal or sublingual route.

20 Claims, No Drawings

ORODISPERSIBLE PHARMACEUTICAL COMPOSITION FOR OROMUCOSAL OR SUBLINGUAL ADMINISTRATION OF AGOMELATINE

The present invention relates to a new coated solid orodispersible pharmaceutical form for the administration of agomelatine by the oral, oromucosal or sublingual route.

Agomelatine or N-[2-(7-methoxy-1-naphthyl)ethyl]acetamide of formula (I):

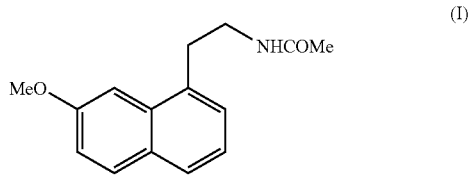

and also its hydrates, crystalline forms and addition salts with a pharmaceutically acceptable acid or base, valuable pharmacological properties: it is a selective agonist of melatoninergic system receptors and, on the other hand, is an antagonist of the 5-HT$_{2C}$ receptor, which confers on it activity in the central nervous system. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent Specifications EP 0 447 285 and EP 1 564 202.

In the following, "agomelatine" is understood to mean agomelatine, and also its hydrates, crystalline forms and addition salts with a pharmaceutically acceptable acid or base.

Agomelatine may be administered by the oral route in the form of immediate-release tablets to be swallowed with half a glass of water. Such agomelatine tablets are of use especially in the treatment of major depression, seasonal affective disorder, sleep disorders, cardiovascular pathologies, pathologies of the digestive system, conditions of insomnia and fatigue resulting from jetlag, appetite disorders and obesity, and all pathologies associated with deregulation of circadian rhythms.

Pharmacokinetic studies in humans have shown that the bioavailability of agomelatine by the oral route is very low in relation to the parenteral route and is subject to variation within one and the same individual and from one individual to another.

Also, the low bioavailability of agomelatine and the variations in inter- and intra-individual concentrations led to the search for a new formulation allowing those problems to be solved. A solid orodispersible pharmaceutical composition of agomelatine described in the patent application EP 1 427 724 was therefore developed containing agomelatine and granules consisting of lactose and starch dried by co-atomisation and marketed under the name STARLAC®. That pharmaceutical composition makes it possible to obtain tablets having a very good capacity to disintegrate in the mouth, while at the same time meeting the orodispersibility criteria. The orodispersible tablets allow the active ingredient to be delivered in the oral cavity. The dissolution of the active ingredient in the saliva and then absorption by the mucous membranes of the oral cavity and rapid entry into the blood makes it possible for pre-systemic degradation to be circumvented. The bioavailability is therefore very clearly improved, with far smaller variabilities and with rapid appearance of the active ingredient in the blood. For optimum absorption through the mucous membranes of the oral cavity, the tablet may be placed specifically under the tongue so as to deliver the active ingredient to the sublingual mucous membrane, which is considered to be the most permeable mucous membrane of the oral cavity.

Moreover, orodispersible pharmaceutical forms are known to improve the compliance and comfort of the patient in view of their rapid disappearance from the oral cavity without the need for liquid and without the problem of swallowing.

It has rapidly become apparent, however, that that formulation has a disadvantage stemming from the active ingredient used, agomelatine, which causes a pronounced irritant sensation in the mucous membranes of the oral cavity.

When the sublingual route is specifically targeted, that stinging effect is exacerbated because of the increased local concentrations of agomelatine, resulting in very poor patient acceptability.

The use of gustatory compounds corresponding to the 5 descriptions sweet, salty, sour, bitter and umami is unlikely to change a perception of pain of the irritation kind since the two chemosensitive systems responsible for the transmission of taste and irritation are anatomically and physiologically different (Franck and Rabin, Nose and Throat Journal, 1989, 68, 291-296). The means known to the person skilled in the art for masking the irritant sensation caused by a product that is intended to be dissolved in the saliva are very limited: (i) the use of local anaesthetics (WO 9915171), (ii) the use of molecules capable of interacting with receptors located on the nerve endings responsible for irritant sensations (Raisinghani and Premkumar, Pain, 2005, 113, 123-133), (iii) desensitization of the nerve endings while maintaining the controlled release (in duration and in amount) of irritant products from pharmaceutical forms that are intended to be kept in the oral cavity for a sustained period U.S. Pat. No. 5,762,963.

Those various approaches have drawbacks, however. Indeed, the use of local anaesthetics or molecules capable of interacting with the receptors implicated in irritant sensation is not satisfactory because those compounds have intrinsic unresearched pharmacological properties. Moreover, a strategy based on desensitization is not compatible with obtaining a pharmaceutical composition that is orodispersible (disintegration in vitro less than 3 minutes), that is to say, that disintegrates in the buccal cavity in less than 3 minutes, and preferably in less than one minute.

The Applicant has now developed a new pharmaceutical composition that allows the irritant problem of the active ingredient to be overcome, while at the same time allowing an orodispersible formulation to be obtained that delivers the active ingredient by the sublingual or oromucosal route and without association with a local anaesthetic or with another pharmacologically active compound.

The present invention relates more especially to a solid pharmaceutical composition composed of:
  a central core or a central layer comprising agomelatine and excipients that allow an orodispersible formulation to be obtained,
  an orodispersible coating.

The pharmaceutical composition according to the invention is formed especially by an orodispersible central core comprising agomelatine, and an orodispersible coating.

One embodiment according to the invention relates to a pharmaceutical composition composed of an orodispersible central layer comprising agomelatine, and an orodispersible coating.

Preferably, the central core or the central layer of the solid pharmaceutical composition according to the invention comprises agomelatine and excipients that allow an orodispersible formulation to be obtained by a compression process using a diluent, a lubricant and, optionally, a flow agent and a disintegrating agent.

More especially, the orodispersible formulation will be obtained with a specific diluent for an orodispersible or with a conventional diluent to which one or more disintegrating agents have been added. Advantageously, the orodispersible diluent used will be based on granules obtained by co-atomisation of lactose and starch and marketed under the name Starlac®, or will be formed by an atomised polyol, such as, for example, sorbitol or mannitol, or by a co-atomised mixture based on polyols, such as, for example, the excipients marketed under the names Partek® or Pharmaburst®.

Other diluents may be used, optionally in association with disintegrants, provided that they impart orodispersible properties with adequate hardness and low friability.

The lubricant, the flow agent and, where applicable, the disintegrating agent are selected from the respective classes of those different excipients. The lubricant is preferably magnesium stearate or sodium stearyl fumarate.

The orodispersible powder coating according to the invention is preferably composed of a diluent, a lubricant, optionally a flow agent, optionally a disintegrating agent and optionally a desensitising agent which is diluted in the coating.

Advantageously, the orodispersible coating according to the invention contains a desensitising agent, such as, for example citric acid, menthol or aspartic acid.

More especially, the orodispersible coating will be obtained with a specific diluent for an orodispersible or with a conventional diluent to which one or more disintegrating agents have been added. Advantageously, the orodispersible diluent used will be based on granules obtained by co-atomisation of lactose and starch and marketed under the name Starlac®, or will be formed by an atomised polyol, such as, for example, sorbitol or mannitol, or by a co-atomised mixture based on polyols, such as, for example, the excipients marketed under the names Partek® or Pharmaburst®.

Other diluents may be used, optionally in association with disintegrants, provided that they impart orodispersible properties with adequate hardness and low friability.

The lubricant, the flow agent and, where applicable, the disintegrating agent are selected from the respective classes of those different excipients. The lubricant is preferably magnesium stearate or sodium stearyl fumarate.

Among the disintegrating agents that can be used in accordance with the invention there may be mentioned those based on sodium glycolate starch, such as, for example, Primojel® or Explotab®, or based on crospovidone, such as, for example, Kollidon®CL, or also those based on L-HPC (low-substituted hydroxypropyl cellulose).

The solid pharmaceutical composition according to the invention is a tablet prepared by a compression coating process. The compression coating process has already been described in the case of non-orodispersible tablets with the aim of devising sustained-release forms: tablets with a central core or multi-layer tablets (Abdul and Poddar, Journal of Controlled Release, 2004, 97, 393-405).

In the case of the coated tablet according to the invention having a central layer, the first coating layer is pre-compressed and constitutes a bed of powder on which the central layer is deposited. The second coating layer covers over the central layer prior to the final step of compression.

In the case of the tablet according to the invention having a central core, the coating by compression requires the use of a central core that is sufficiently resistant to support the coating step. Such a coating process is not recommended, a priori, in the case of orodispersible cores generally exhibiting a moderate resistance to crushing and a non-negligible friability. In the case of the present invention, the central core can be coated by compression without any difficulty using a conventional industrial compression press suitable for compression coating.

The present invention thus also relates to a process for obtaining the solid orodispersible tablet having a central core, which process is characterised in that the constituents of the central core are mixed and then compressed, and then the constituents of the coating layer are mixed, and coating is carried out by compression of the resulting powder mixture around the core.

The Applicant, then, has found that the pharmaceutical composition according to the invention retains its orodispersible character with a very good capacity to disintegrate in the mouth, which was not, a priori, foreseeable for a coated pharmaceutical composition. In particular, the pharmaceutical composition according to the invention makes it possible to achieve disintegration in the oral cavity in less than 3 minutes, and more especially in less than one minute, without the need for a controlled release capable of acting on the mechanisms of desensitization. Surprisingly, the orodispersible pharmaceutical composition according to the invention allows very good acceptability of the active ingredient to be achieved by limiting its irritant character, while at the same time enabling the active ingredient to be dissolved in the saliva and allowing its rapid entry into the blood.

The pharmaceutical composition according to the invention, administered by the sublingual route, has also demonstrated an excellent capacity to reduce the irritant sensation caused by the active ingredient, and thus excellent patient acceptability. Administration carried out in that way enables the hepatic first-pass effect to be limited, and thus allows the bioavailability of the active ingredient to be increased and the inter-individual variation, observed with conventional agomelatine pharmaceutical compositions intended for enteral administration, to be decreased.

The pharmaceutical compositions according to the invention are preferably characterised in that they comprise, in relation to the total weight of the tablet:
from 0.02% to 5% by weight of agomelatine
from 70% to 99.88% by weight of Starlac® or mannitol for direct compression
from 0.1% to 3% by weight of magnesium stearate.

Even more especially, the pharmaceutical compositions comprise, in relation to the total weight of the tablet:
from 0.02% to 5% by weight of agomelatine
from 70% to 99.88% by weight of Starlac® or mannitol for direct compression
from 0.1% to 3% by weight of magnesium stearate
from 0.5% to 5% by weight of a desensitizing agent, preferably citric acid, and preferably from 1% to 3%.
They will optionally contain:
a lubricant other than magnesium stearate, such as, for example, from 0.1% to 3% by weight of sodium stearyl fumarate, preferably from 0.5% to 1.5%;
a flow agent, such as colloidal silica, for example, from 0.1% to 3% by weight, preferably from 0.2% to 1%;
from 0.01% to 5% by weight of one or more sweetening agents, preferably from 0.1% to 1%.

In addition, the pharmaceutical compositions according to the invention may contain flavouring compounds, colouring substances and one or more sweetening agents such as saccharose, aspartame, acesulfame or sucralose.

The dosage used is adaptable according to the nature and the severity of the disorder, the administration route and the age and weight of the patient. The dosage varies from 0.1 mg to 1 g of agomelatine per day in one or more administrations.

The Examples below illustrate the invention but do not limit it in any way:

EXAMPLE 1

Formulation

Finished Tablet of 320 mg

| Constituents | Amount (mg) |
|---|---|
| Central core | |
| Agomelatine | 1 |
| Starlac ® | 67.65 |
| Sodium stearyl fumarate | 1.35 |
| Coating | |
| Powdered anhydrous citric acid | 7.5 |
| Starlac ® | 238.75 |
| Acesulfame potassium | 2.5 |
| Sodium stearyl fumarate | 1.25 |

EXAMPLE 2

Formulation

Finished Tablet of 350 mg

| Constituents | Amount (mg) |
|---|---|
| Central core | |
| Agomelatine | 1 |
| Starlac ® | 48.75 |
| Magnesium stearate | 0.25 |
| Coating | |
| Powdered anhydrous citric acid | 10 |
| Starlac ® | 282 |
| Aspartam | 3 |
| Acesulfame potassium | 3 |
| Magnesium stearate | 2 |

The central core is prepared by mixing the constituents followed by direct compression. The hardness of the cores of Examples 1 and 2 is about 15 Newtons with a friability of less than 1%. The constituents of the coating layer are mixed and then coating is carried out by compressing the resulting powder mixture around the cores.

The coated tablets of Examples 1 and 2 have a target hardness of 40 Newtons and a friability of about 1%. The in vitro disintegration times are less than 3 minutes (European Pharmacopoeia).

EXAMPLE 3

Formulation

Finished Tablet of 320 mg

| Constituents | Amount (mg) |
|---|---|
| Central core | |
| Agomelatine | 1 |
| Mannitol for direct compression | 68.3 |
| Magnesium stearate | 0.7 |
| Coating | |
| Powdered anhydrous citric acid | 7.5 |
| Mannitol for direct compression | 235 |
| Acesulfame potassium | 2.5 |
| Aspartam | 2.5 |
| Magnesium stearate | 2.5 |

EXAMPLE 4

Formulation

Finished Tablet of 320 mg

| Constituents | Amount (mg) |
|---|---|
| Central layer | |
| Agomelatine | 2 |
| Starlac ® | 67.65 |
| Magnesium stearate | 0.35 |
| Coating (2 outer layers of 125 mg each) | |
| Powdered anhydrous citric acid | 7.5 |
| Starlac ® | 238.75 |
| Sucralose | 2.5 |
| Magnesium stearate | 1.25 |

The constituents of the different layers are mixed using a mixer by tumbling, and the powder mixtures obtained are then placed in the feed hoppers of a compression machine comprising a plurality of compression stations. The first layer of coating (125 mg) is pre-compressed and constitutes a bed of powder on which the central layer is deposited. The second layer of coating covers over the central layer prior to the final step of compression. The coated tablets obtained have a target hardness of 40 Newtons and a friability of about 1%. The in vitro disintegration times are less than 3 minutes (European Pharmacopoeia).

EXAMPLE 5

Acceptability

An acceptability study was carried out in 12 healthy male volunteers by administering in a single dose either a conventional orodispersible composition containing 3% citric acid and 1 mg agomelatine diluted in the mass (finished uncoated orodispersible tablet of 320 mg), or a finished orodispersible tablet of 320 mg having a central core and containing 1 mg of agomelatine in the core and 3% citric acid in the coating. The study carried out showed that the coated orodispersible tablet was liked well or moderately by 67% of the volunteers as compared with only 50% for the conventional orodispersible tablet.

The invention claimed is:

1. A coated solid orodispersible pharmaceutical composition comprising:
    a central core or a central layer comprising agomelatine and excipients allowing an orodispersible formulation to be obtained,
    an orodispersible coating.

2. The composition according to claim 1, wherein agomelatine is obtained as the crystalline II form.

3. The composition according to claim 1, wherein the composition contains a central core.

4. The composition according to claim 1, wherein the composition contains a central layer.

5. The composition according to claim 1, wherein the central core or layer comprises a diluent imparting an orodispersible property.

6. The composition according to claim 5, wherein the diluent used in the central core comprises granules obtained by co-atomisation of lactose and starch.

7. The composition according to claim 1, wherein the central core or layer comprises a diluent and a disintegrating agent.

8. The composition according to claim 1, wherein the orodispersible coating comprises a diluent imparting an orodispersible property.

9. The composition according to claim 8, wherein the diluent used in the coating comprises granules obtained by co-atomisation of lactose and starch.

10. The composition according to claim 1, wherein the orodispersible coating comprises a desensitising agent.

11. The composition according to claim 10, wherein the desensitising agent used is citric acid.

12. The composition according to claim 1, comprising, in relation to the total weight of the composition:
    from 0.02% to 5% by weight of agomelatine
    from 70% to 99.88% by weight of granules obtained by co-atomisation of lactose and starch or mannitol for direct compression
    from 0.1% to 3% by weight of magnesium stearate.

13. The composition according to claim 1, comprising, in relation to the total weight of the composition:
    from 0.02% to 5% by weight of agomelatine
    from 70% to 99.88% by weight of granules obtained by co-atomisation of lactose and starch or mannitol for direct compression
    from 0.1% to 3% by weight of magnesium stearate
    from 0.5% to 5% by weight of a desensitizing agent.

14. The composition according to claim 1, further comprising one or more lubricants, and also a flow agent, and one or more sweetening agents.

15. The composition according to claim 1, wherein the composition is in the form of a tablet having a central core.

16. The composition according to claim 1, wherein the composition is in the form of a three-layer tablet.

17. A process for preparing the composition according to claim 15, wherein the constituents of the core are mixed and then compressed by direct compression, and then the constituents of the coating layer are mixed and the coating is carried out by compression of the resulting powder mixture around the cores.

18. A process for the manufacture of a coating for the coated solid orodispersible composition having a central core or central layer comprising agomelatine according to claim 1, wherein the coated solid orodispersible composition disintegrates in the mouth in less than three minutes, wherein citric acid is mixed with granules consisting of lactose and starch dried by co-atomisation.

19. A process for the manufacture of a coating for the coated solid orodispersible composition having a central core or central layer comprising agomelatine according to claim 1, wherein the coated solid orodispersible composition disintegrates in the mouth in less than one minute, wherein citric acid is mixed with granules consisting of lactose and starch dried by co-atomisation.

20. A method for treating a living animal body, including a human, afflicted with a condition selected from major depression, seasonal affective disorder, sleep disorders, cardiovascular pathologies, pathologies of the digestive system, conditions of insomnia and fatigue resulting from jetlag, appetite disorders and obesity, and pathologies associated with deregulation of circadian rhythms, comprising the step of administering to the living animal body, including a human, a composition according to claim 1 which is effective for treatment of the condition.

* * * * *